(12) United States Patent
Da Costa et al.

(10) Patent No.: US 11,110,832 B2
(45) Date of Patent: Sep. 7, 2021

(54) AUTOMOBILE SEAT AND METHOD FOR MANAGEMENT OF THE COMFORT OF AN OCCUPANT OF SUCH A SEAT

(71) Applicant: Faurecia Sièges d'Automobile, Nanterre (FR)

(72) Inventors: Anne-Isabelle Da Costa, Etrechy (FR); Samuel Baudu, Boulogne Billancourt (FR)

(73) Assignee: FAURECIA SIÈGES D'AUTOMOBILE, Nanterre (FR)

( * ) Notice: Subject to any disclaimer, the term of this patent is extended or adjusted under 35 U.S.C. 154(b) by 169 days.

(21) Appl. No.: 15/610,132

(22) Filed: May 31, 2017

(65) Prior Publication Data

US 2017/0341549 A1    Nov. 30, 2017

(30) Foreign Application Priority Data

May 31, 2016    (FR) ...................................... 16 54888

(51) Int. Cl.
| | |
|---|---|
| *B60N 2/56* | (2006.01) |
| *A61B 5/145* | (2006.01) |
| *B60N 2/90* | (2018.01) |
| *B60N 2/00* | (2006.01) |
| *A61B 5/01* | (2006.01) |
| *A61B 5/18* | (2006.01) |
| *A61B 5/00* | (2006.01) |

(52) U.S. Cl.
CPC .................. *B60N 2/56* (2013.01); *A61B 5/01* (2013.01); *A61B 5/14517* (2013.01); *A61B 5/18* (2013.01); *A61B 5/4266* (2013.01); *A61B 5/6893* (2013.01); *B60N 2/002* (2013.01); *B60N 2/5621* (2013.01); *B60N 2/5678* (2013.01); *B60N 2/976* (2018.02); *A61B 2562/0247* (2013.01)

(58) Field of Classification Search
CPC ........ B60N 2/56; B60N 2/976; B60N 2/5678; B60N 2/002; B60N 2/5621; A61B 5/4266; A61B 5/14517; A61B 5/01; A61B 5/18; A61B 5/6893; A61B 2562/0247
See application file for complete search history.

(56) References Cited

U.S. PATENT DOCUMENTS 3,954,100 A * 5/1976 Sem-Jacobsen ... A61B 5/04085
600/393
6,291,803 B1 * 9/2001 Fourrey ................... B60N 2/58
219/202

(Continued)

FOREIGN PATENT DOCUMENTS

| EP | 2910413 A1 | 8/2015 |
|---|---|---|
| JP | H04285528 A | 10/1992 |

(Continued)

OTHER PUBLICATIONS

French Preliminary Search Report in French with English translation for application No. FR1654888, dated Jan. 23, 2017, 12 pages.

*Primary Examiner* — Milton Nelson, Jr.
(74) *Attorney, Agent, or Firm* — Reising Ethington P.C.

(57) ABSTRACT

A vehicle seat has at least one occupant comfort actuator suited for acting on a part of the body of an occupant of the seat. The actuator is driven based on at least one measurement of one sensor of sweat from the occupant of the seat.

14 Claims, 2 Drawing Sheets

(56) References Cited

U.S. PATENT DOCUMENTS

| | | | | |
|---|---|---|---|---|
| 6,353,394 | B1* | 3/2002 | Maeda | B60N 2/002 |
| | | | | 177/144 |
| 7,152,920 | B2* | 12/2006 | Sugiyama | B60N 2/002 |
| | | | | 297/284.6 |
| 2002/0123704 | A1* | 9/2002 | Hori | A61B 5/4035 |
| | | | | 601/99 |
| 2003/0220766 | A1* | 11/2003 | Saunders | B60R 21/01516 |
| | | | | 702/173 |
| 2006/0244289 | A1* | 11/2006 | Bedro | B60N 2/5621 |
| | | | | 297/180.1 |
| 2008/0256967 | A1* | 10/2008 | Errington | B60H 1/00742 |
| | | | | 62/244 |
| 2009/0193814 | A1* | 8/2009 | Lofy | B60N 2/5692 |
| | | | | 62/3.61 |
| 2012/0071799 | A1* | 3/2012 | Inada | A61H 9/0078 |
| | | | | 601/98 |
| 2012/0212353 | A1* | 8/2012 | Fung | B60W 10/22 |
| | | | | 340/905 |
| 2014/0275834 | A1* | 9/2014 | Bennett | A61B 5/6893 |
| | | | | 600/301 |
| 2015/0057515 | A1* | 2/2015 | Hagen | G01N 27/3273 |
| | | | | 600/346 |
| 2018/0263539 | A1* | 9/2018 | Javey | A61B 5/6833 |

FOREIGN PATENT DOCUMENTS

| | | |
|---|---|---|
| KR | 20140028255 A | 3/2014 |
| WO | WO2015033070 A1 | 3/2015 |
| WO | WO2016061362 A2 | 4/2016 |

* cited by examiner

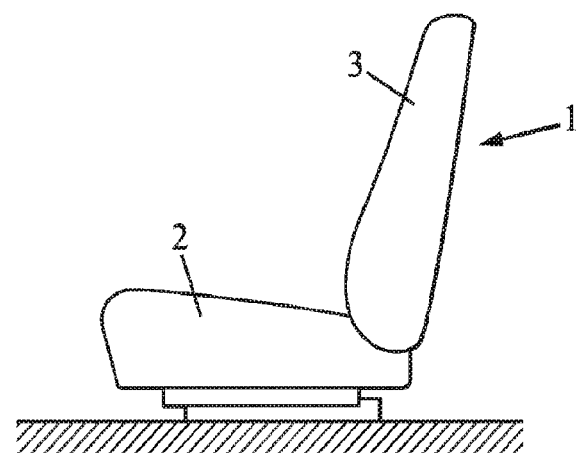
FIG. 1
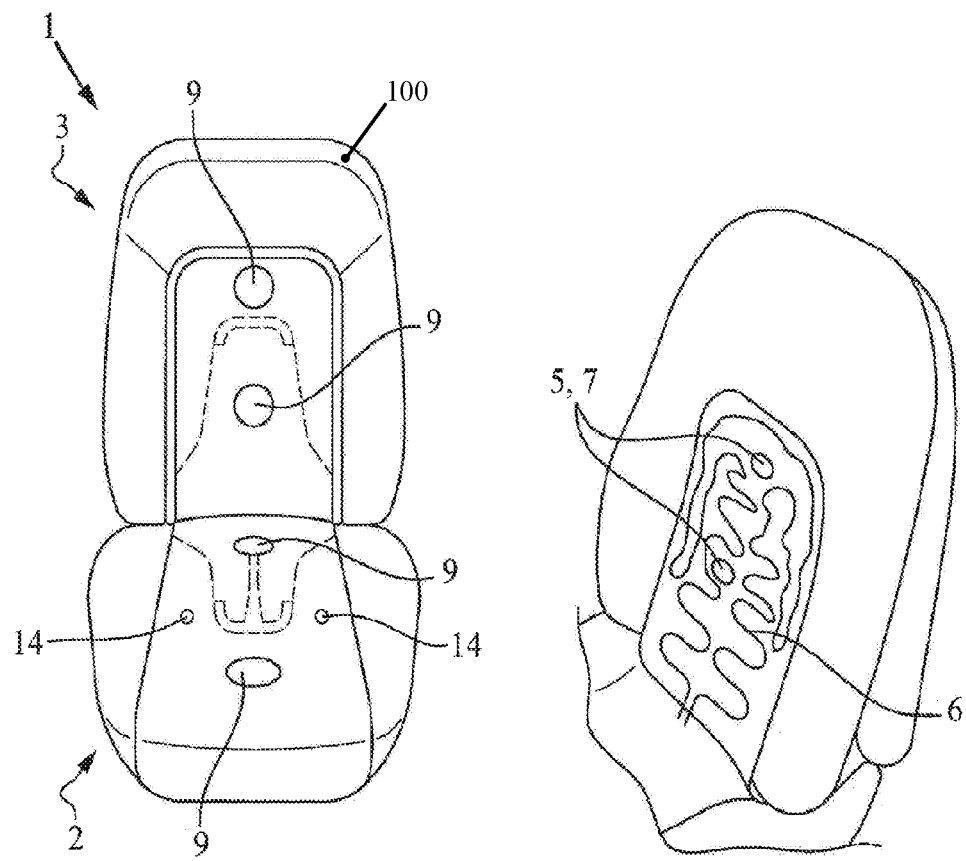
FIG. 2
FIG. 3

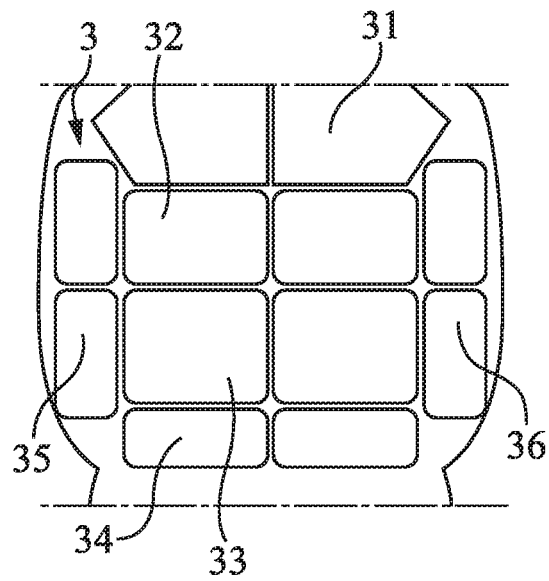
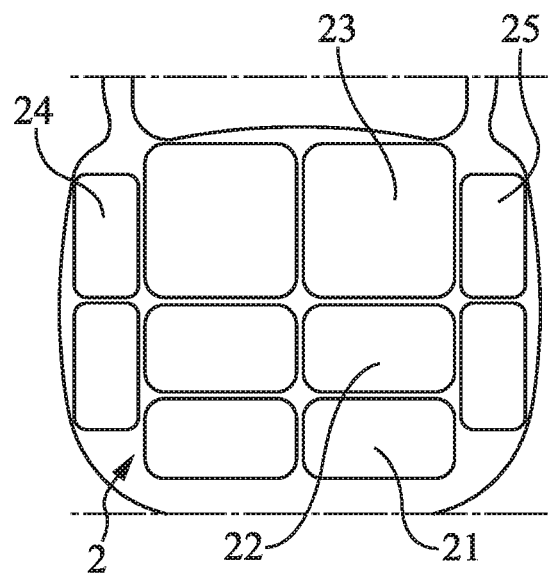
FIG. 4A    FIG. 4B
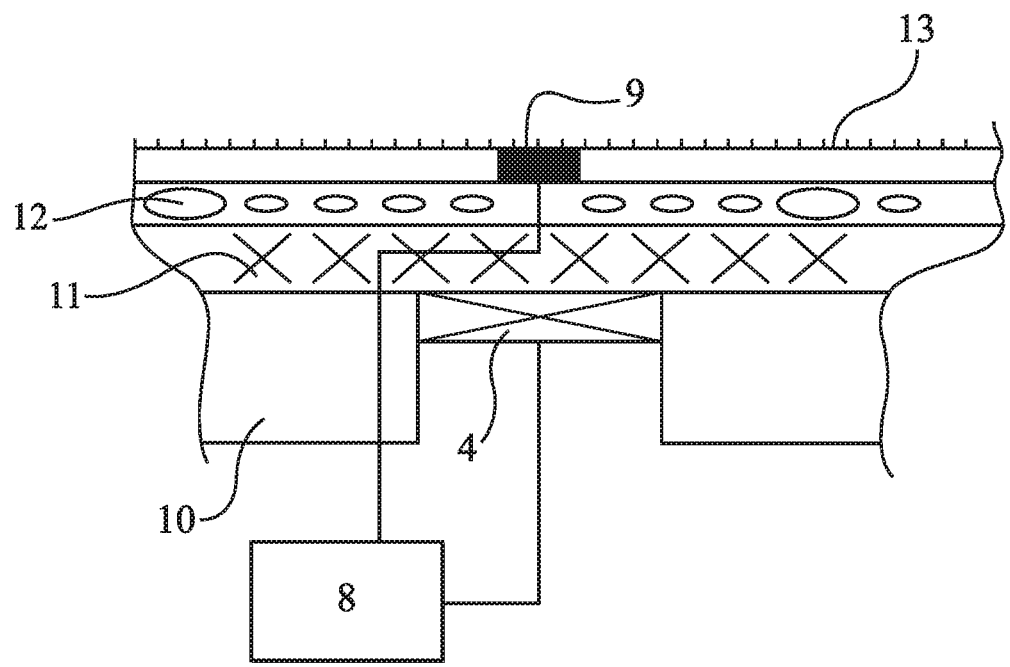
FIG. 5

AUTOMOBILE SEAT AND METHOD FOR MANAGEMENT OF THE COMFORT OF AN OCCUPANT OF SUCH A SEAT

TECHNICAL FIELD

The present invention relates to automobile seats.

BACKGROUND

In order to improve the comfort of the occupant of an automobile, seats are known that are provided with means for climate control arranged for providing heating or ventilation near the surface of the seat in contact with which the occupant of the seat positions himself Such seats comprise temperature or humidity sensors arranged near the surface of the seat for controlling the means of climate control.

However, one disadvantage of such a seat is that the temperature and humidity measures necessarily depend on exterior parameters, for example, the ambient climate in which the occupant is located. It is therefore necessary to have an ambient temperature or humidity sensor in order to compare the measurements from the sensors placed in the seat with a reference measurement. The result of this is a more complex control of the means of climate control of the seat.

SUMMARY

An aim of the present invention is to at least resolve this disadvantage. More precisely, one aim of the present invention is to provide a simple device with which to improve the comfort of the occupant of the seat.

Thus, the invention relates to a vehicle seat comprising at least one means of action suited for acting on a part of the body of an occupant of the seat, wherein the means of action is driven or otherwise controlled based on at least one measurement of one sensor of sweat from the occupant of the seat.

Because of the driving of the means of action based on the measurement of sweat from the occupant, a more reliable control of comfort can be obtained, in particular independent of the ambient conditions independent of the occupant.

In various embodiments of the invention, use could furthermore be made of one or more of the following dispositions:

- The seat comprises a plurality of means of action, wherein the means of action are disposed in individualized seat surface areas;
- The individualized seat surface areas correspond respectively to various parts of the body of an occupant;
- The measurement of the sweat from the occupant of the seat is done with at least one sweat sensor disposed in the seat;
- The measurement of the sweat from the occupant of the seat is done with at least one sweat sensor disposed directly in contact with the skin of the occupant;
- The sweat sensor is suited for independently measuring at least one first biomarker and one second biomarker;
- The first biomarker is characteristic of an excess of body heat from the occupant, and the second biomarker is characteristic of a stress of the occupant;
- The means of action is a means of ventilation, a means of heating, a means of cooling and/or a means of massage; and
- The seat comprises a presence sensor, wherein the means of action is driven based on the measurement from the presence sensor.

The invention also relates to a method for management of the comfort of an occupant of the seat, comprising the steps of:

- getting at least one measurement from one sensor of sweat from an occupant of the seat; and
- driving or otherwise controlling at least one means of action based on the measurement of sweat from the occupant of the seat.

According to an implementation, the means of action is driven based on a biomarker measured by the sweat sensor.

According to another implementation, a plurality of means of action is driven based on the measurement from the sensor of sweat from the occupant of the seat wherein the means of action are disposed in various individualized seat surface areas.

Of course, the various characteristics, variants and/or embodiments of the present invention can be combined with each other according to various combinations in so far as they are not incompatible or exclusive with each other.

BRIEF DESCRIPTION OF THE DRAWINGS

The present invention will be better understood and other characteristics and advantages will again appear upon reading the following detailed description comprising an embodiment given for illustration with reference to the attached figures, presented as nonlimiting examples, which will serve to supplement the understanding of the present invention and the disclosure of the implementation thereof and, as necessary, contribute to the definition thereof, in which:

FIG. 1 is a schematic side view of a vehicle seat according to an embodiment of the present invention;

FIG. 2 is a front view of the vehicle seat from FIG. 1;

FIG. 3 is a perspective view of the back of the vehicle seat from FIG. 1;

FIGS. 4a and 4b are views of individualized areas of respectively the seatback and the seat cushion from FIG. 1; and FIG. 5 is a partial section view of the seat cushion or seatback from FIG. 1.

DETAILED DESCRIPTION

It should be noted that, in the figures, the structural and/or functional elements common to the various embodiments can have the same references. In that way, unless indicated otherwise, such elements may have identical structural, dimensional and material properties.

In the interest of clarity, only the elements useful for understanding the embodiments described have been shown and will be described in detail.

In the following description, when reference is made the absolute position qualifiers, such as the terms 'front', 'rear', 'top', 'bottom', 'left', 'right', etc., or relative such as the terms 'above', 'below', 'upper', 'lower', etc., or orientation qualifiers, reference is made to a seat in the normal position for use thereof in the direction of ordinary progression of the vehicle.

FIG. 1 shows an automobile vehicle seat 1 having a seat cushion 2 and a seatback 3 intended to receive an occupant of the seat 1 in sitting position.

The seat 1 according to the invention, in particular the seat cushion 2 and the seatback 3, comprise at least one means of action 4 on the occupant of the seat 1. Means of action is understood to be an actuator or other element suited for acting on the occupant of the seat 1 in order to improve their comfort, in particular when the occupant is in a seated position in the seat 1.

According to an implementation, the means of action 4 is a means of climate control 5.

The means of climate control is, for example, a means of ventilation 5, also called fan 5. The fan 5 circulates air around the seat 1. The fan 5 can consist of an aspiration of air, a blowing of air or a combination of aspiration and blowing of air in alternation or simultaneous.

According to another embodiment, the means of action 4 is a means of heating and/or a means of cooling 6.

A means of heating 6 is advantageously formed of an electrical resistance. The means of heating and/or cooling 6 can however be implemented by any other well-known element.

According to another implementation, the means of action 4 is a means of massage 7.

The means of massage 7 is suited to massage a localized portion of the body of the occupant. The means of massage 7 can, for example, consist of locally and temporarily deforming the surface of the seat 1. For example, the means of massage 7 can be rigid elements located in the seat 1 and suited for performing a repeated movement with which to massage a portion of the body of the occupant when the occupant is in seated position in the seat 1.

The examples of the means of action 4 given above are purely illustrative and other means of action 4 can be conceived for improving the comfort of the occupant of the seat 1. Additionally, the various types of means of action 4 can be combined in a single seat 1. The seat 1 can also include a single type of means of action 4 disposed in various locations of the seat 1.

In particular, FIG. 3 shows an embodiment in which the seatback 3 comprises a means of heating and/or cooling 6 and also localized means of ventilation 5 and or massage 7.

The one or more means of action 4 of the seat 1 are connected to a control unit 8.

The control unit 8, is, for example, an electronic control mechanism comprising, in particular, an electronic control circuit. The control unit 8 can in that way be specific to one seat 1 or manage the control of several seats. The control unit 8 can be combined or incorporated in a control unit managing the entire vehicle. The control unit 8 is suited for driving means of action 4 advantageously independently of each other.

The means of action 4 are preferably disposed in several individualized surface areas of the seat. Surface of the seat includes the visible surface of the seat 1 with which the occupant comes into contact, but also the neighboring surfaces such as the lateral upholstery, etc.

Each individualized area is suited for comprising at least one means of action 4. The location of the means of action 4 in each area serves to manage the comfort of the occupant more precisely and with greater responsiveness.

As more specifically shown in FIG. 4A which shows a schematic representation of a sample distribution of the various individualized surface areas of the seatback 3 of the seat 1, the surface of the seatback 3 can be divided into several individualized surface areas of the seat 1.

In that way, according to the example from FIG. 4A, the seatback 3 comprises, along a vertical direction, from top to bottom:

At least one upper area 31, which advantageously corresponds to an area for supporting the shoulders of the occupant of the seat 1;

At least one intermediate area, which advantageously corresponds to an area for supporting the torso of the occupant of the seat 1; and At least one lower area 34, which advantageously corresponds to an area located near the pelvis of the occupant of the seat 1.

The intermediate area can comprise:

A first intermediate area 32, which advantageously corresponds to an area located near the rib cage of the occupant of the seat 1; and A second intermediate area 33, which corresponds to an area for supporting the lower back of the occupant of the seat 1.

Additionally, the seatback 1 can comprise at least one lateral area 35, 36, preferably two lateral areas 35, 36 disposed on each side of the seatback 1. The lateral areas 35, 36 correspond to lateral upholstery of the seatback 1.

As more specifically shown in FIG. 4B which shows a schematic representation of a sample distribution of the various individualized surface areas of the seat cushion 2 of the seat 1, the surface of the seat cushion 2 can be divided into several individualized surface areas of the seat.

In that way, according to the example from FIG. 4B, the seat cushion 2 comprises, along a longitudinal direction from front to back:

At least one front area 21, which advantageously corresponds to an area located near the front edge of the cushion of the seat 1;

At least one intermediate area 22, which advantageously corresponds to an area for support of the thighs of the occupant of the seat 1; and At least one rear area 23, which advantageously corresponds to an area for supporting the butt of the occupant of the seat 1.

Additionally, the seat cushion 2 can comprise at least one lateral area 24, 25, preferably two lateral areas 24, 25 disposed on each side. The lateral areas 24, 25 correspond to lateral upholstery of the seat cushion 2.

According to an implementation, the seat 1 comprises at least one means for detection of sweat 9, also called sweat sensor 9.

A sweat sensor 9 is suited for measuring a level of sweat from the occupant of the seat 1, in particular when the occupant is located in seated position on the seat 1.

In that way, the sweat sensor 9 allows detection of the sweat from the occupant which serves to determine the moment of arrival and then the presence of the occupant on the seat 1.

The sweat sensor 9 can also additionally serve to quantify the sweat from the occupant.

Furthermore, the sweat sensor 9 is suited for determining the origin of the sweat from the occupant of the seat 1. In particular, the sweat sensor 9 is suited for determining whether the sweat from the occupant is due to an excess of body heat, stress, fatigue of the occupant, etc.

In particular, the sweat sensor 9 is suited for measuring one or more biomarkers contained in the sweat of the occupant. The biomarker can be a liquid or gaseous component.

The biomarker from the sweat can, for example, be an electrolyte such as sodium, chloride, potassium or calcium ions.

The biomarker can be a metabolite, such as lactate, creatinine, glucose and uric acid.

The biomarker can be an amino acid, dehydroepiandrosterone (DHEA), cortisol or orexine-A.

The biomarker can be a protein, such as interleukines, a tumor necrosis factor and a neuropeptide.

Advantageously, the sweat can be related to an excess of heat and can come from eccrine sweat glands. The sweat generated then mainly comprises water and salt.

The sweat can advantageously be stress related and can come from apocrine glands. The sweat generated is then often acidic and fatty.

In that way, the sweat sensor 9 is suited for detecting a liquid or gaseous stress-related component, in particular an odor, for example.

The sweat sensor 9 can also be suited for measuring a heart rhythm, in particular for measuring the stress of the occupant.

According to an implementation, the sweat sensor 9 is suited for measuring the sweat coming from apocrine glands for measuring the stress of the occupant.

According to another implementation, the sweat sensor 9 is suited for measuring a biomarker and a heart rhythm for measuring the stress of the occupant.

According to another implementation, the sweat sensor 9 is suited for measuring a biomarker in liquid form and a heart rhythm for measuring the stress of the occupant.

According to another implementation, the sweat sensor 9 is suited for measuring a biomarker in gaseous form and a heart rhythm for measuring the stress of the occupant.

The stress-related biomarker measured by the sweat sensor 9 advantageously comes from apocrine glands.

The sweat sensor 9 is advantageously connected to the control unit 8. The one or more means of action 4 can then be advantageously driven independently by the control unit 8 based on the measurement from the sweat sensor 9.

In the embodiment shown in FIG. 2, the seatback 3 comprises two sweat sensors 9. The seat cushion 2 also comprises two sweat sensors 9.

Nonetheless, the embodiment shown by FIG. 2 is purely illustrative and the seatback 3 and/or the seat cushion 2 could comprise a different number or location of sweat sensors 9 in the seat 1. In particular, each individualized area or some individualized areas of the seat 1 can comprise a sweat sensor 9.

The distribution of sweat sensors 9 in the seat 1 can serve to determine the position of the occupant on the seat 1 since the local detection of sweat indicates the presence of a part of the body of the occupant in contact with the seat 1.

Since it is possible in that way to individually detect the presence of a contact with the occupant of the seat in various locations of the seat or at least in some locations of the seat—for example, the rear area 23 of the seat cushion 2 or the lower area 34 the seatback 3—an indication of the presence of the occupant and/or an indication of the position of the occupant, for example, head upright or slumped position, can be obtained.

Because of the distribution of sweat sensors 9 in various areas of the surface of the seat, and because of the individualization for each area of measures obtained by these various sensors 9, a state of the sweating of the occupant in each surface area can also be determined. The means of action 4 of each area can then be driven based on measurements provided by the sweat sensors 9.

Furthermore, because of the independent control of the means of action 4 in each individualized area, the energy consumption needed for the comfort of the occupant is minimized. Thus, only the means of action 4 locally needed are driven and the areas not needing specific action are inactive and therefore do not need any energy.

FIG. 5 shows a local section view of the seat cushion 2 or the back 3 of the seat 1. More precisely, FIG. 5 shows a sample arrangement of a means of action 4 and a sweat sensor 9 in a seat 1.

As shown in FIG. 5, the seat 1 comprises a padding 10, in particular a seatback padding and a seat cushion padding.

The seat 1 comprises a structural layer 11, preferably directly in contact with the padding 10 of the seat 1. The structural layer 11 is a layer made of a material with which to maintain an area of air circulation even when the seat is occupied. Advantageously, the structural layer 11 has a limited amount of compression in order to allow air circulation.

The structural layer 11 is topped by a foam layer 12, preferably a perforated foam layer 12. The foam layer 12, in particular the perforated foam layer 12, also allows air circulation.

Additionally, the seat 1 comprises a seat cover 13 arranged above the padding 10 of the seat 1, more specifically above the structural layer 11 and/or the foam layer 12.

As shown on FIG. 5, the sweat sensor 9 is preferably placed above the foam layer 12. More specifically, the sweat sensor 9 is placed under the seat cover 13. With such an arrangement, the sweat sensor 9 is disposed closest to the surface of the seat 1 and therefore to the occupant of the seat.

As shown in FIG. 5, the means of action 4 is placed in the padding 10 of the seat 1. The means of action 4 can then be a fan 5. The assembly composed of the structural layer 11 and the foam layer 12 allows passage and distribution of air circulated by the fan 5.

In a variant not shown in the figures, the means of action 4 can be placed directly under the seat cover 13, or else placed above the foam layer 12. The means of action 4 can then be a means of heating and/or cooling 6 or a means of massage 7.

A method is described below for management of the comfort of an occupant of the seat 1 according to an embodiment of the invention.

In a first step, the sweat of the occupant of the seat 1 is detected.

The sweat sensor 9 is preferably disposed in the seat 1 as described above. According to this implementation, if the measurement value from the sweat sensor 9 quickly changes, it can be considered that an occupant is found in seated position in the seat 1. According to an implementation in which the seat 1 comprises a plurality of sweat sensors 9, it is also possible to determine the position of the occupant on the seat 1.

However, the detection of the sweat from the occupant can also be done by any other means, independent of the seat 1 of the occupant.

Thus, according to an implementation, the sweat sensor can consist of a mechanism directly arranged in bodily contact with the occupant, such as a body patch. The sweat sensor can also be a portable device, such as a portable telephone, for example. The device then communicates with the control unit 8 by a wired or wireless connection.

According to another implementation, the sweat sensor can be a contactless detector, for example optical. The sweat sensor serves to detect the sweat of an occupant remotely, for example. on the face. Such a detector can, for example, function by passive thermal imaging.

More generally, it is possible to combine several sweat sensors depending on several different means in order to obtain one or more sweat measurements for the occupant.

The sweat sensor 9 measures the quantity of sweat and/or the biomarkers from the sweat of the occupant.

In a second step, the sweat sensor 4 sends the measurement to the control unit 8.

In a third step, the control unit 8 drives (operates) the one or more means of action 4 based on the type and/or quantity of sweat detected by the one or more sweat sensors 9.

Operation of the means of action 4 by the control unit 8 is preferably automatic. The control of the means of action 4 depending in particular on measurements from the one or more sweat sensors 9 can be determined with a driving algorithm.

For example, the control unit 8 can trigger driving of a means of action 4 if the quantity of sweat exceeds the threshold value or goes through quick changes over time. The algorithm can also consider other external data or data specific to the occupant in order to determine the driving of the means of action 4. For example, such an algorithm can specify that the seatback 1 be heated more than the seat cushion 2 and that the temperature felt over the entire surface of the seat be homogeneous.

However, additionally, a manual control mode for the control unit 8 is also possible.

The control of the means of action 4 may be based on the measurement from the sweat sensor 9.

As an example, if a stress specific biomarker can be detected with the sweat sensor 9, the control unit 8 drives a means of massage 7 so as to relax the occupant. If a biomarker specific to excess heat can be detected with the sweat sensor 9, the control unit drives a means of climate control, such as a fan 5 or a means of cooling 6 so as to reduce the body heat from the occupant.

It is also possible to arrange a sensor 100 with which to measure the ambient temperature and/or humidity (as shown in FIG. 2). The sensor 100 for measurement of the ambient temperature and/or humidity is advantageously arranged in the seat 1. The sensor 100 for the ambient temperature and/or humidity is then connected to the control unit 8.

The triggering or the speed of the means of action 4, for example of the means of climate control 5, are then adjusted, preferably in real time, depending on the ambient temperature and/or humidity level measured by the ambient temperature and/or humidity sensor.

Because of the distribution of several sweat sensors 9 in various areas of the surface of the seat 1, and because of the individualization for each area of measures obtained by these various sensors 9, a state of sweating in each area of surface can be determined, and the means of action 4 for each area can be independently controlled depending on the values provided by the sensors. The occupant can thus be helped to find and maintain a state of optimal comfort.

For example, an excess of sweat on some parts of the body of the user, for example in the lumbar region, can be compensated locally by increased ventilation while also considering different thermal and/or airflow needs in other parts of the body requiring, for example, more heat.

The control of the means of action 4 in each area can also depend on sweat sensors 9 in other areas. The situation of neighboring areas can be considered, for example to avoid the occupant having the sensation of heavy ventilation in one area and no ventilation in an adjacent area.

When the values provided by the sweat sensors 9 suggests that the occupant has found an adequate comfort level, in particular an acceptable value of sweating, the means of action 4 are stopped, preferably automatically.

The seat 1 can also include at least one presence sensor 14 for detecting the presence of the occupant, advantageously distinct from the sweat sensor 9. The presence sensor 14 can for example be a pressure sensor, capacitive sensor, or even any other type of sensor.

The presence sensor 14 can for example be located in the seat cushion 2. As shown in FIG. 2, it is also conceivable to have several presence sensors 14 distributed in various individualized locations or areas of the seat 1, in that way allowing better identification of the position of the occupant the seat 1.

The presence sensors, such as a pressure sensor 14, can supplement the position detection done by means of the sweat sensor 9, since it can then be considered that a detection of an exerted pressure is an indication of the presence of the occupant.

With the measurement from the presence sensors 14, the means of action 4 in each area of the seat 1 can then also be controlled depending on the morphology or position of the occupant in the seat 1.

Obviously, the invention is not limited to the embodiments previously described and provided solely as an example. It encompasses various modifications, alternative forms and other variants which the person skilled in the art could conceive in the context of the present invention and in particular any combination of different embodiments previously described which can be taken separately or in combination.

The invention claimed is:

1. A seat for a vehicle, comprising at least a climate controller and a massager suited for acting on a part of a body of an occupant of the seat,
   wherein at least the climate controller and the massager are operated based on at least one measurement of at least one biomarker contained in sweat from the occupant by at least one sensor of sweat,
   wherein the at least one sensor of sweat is configured for independently measuring at least one first biomarker among said at least one biomarker and at least one second biomarker among said at least one biomarker, said at least one first biomarker and said at least one second biomarker being contained in the sweat from the occupant, wherein the at least one first biomarker is characteristic of an excess of body heat from the occupant, and the at least one second biomarker is characteristic of a stress of the occupant, and
   wherein the climate controller is operated when said at least one first biomarker is detected and wherein the massager is operated when said at least one second biomarker is detected.

2. The seat according to claim 1, comprising a plurality of means of action, wherein the means of action are disposed in individualized seat surface areas.

3. The seat according to claim 2, wherein the individualized seat surface areas correspond respectively to various parts of the body of the occupant.

4. The seat according to claim 1, wherein the at least one sensor of sweat is disposed in the seat.

5. The seat according to claim 1, wherein the at least one sensor of sweat is adapted to be disposed directly in contact with the skin of the occupant.

6. The seat according to claim 1, wherein the climate controller includes at least one of a means of ventilation, a means of heating, or a means of cooling.

7. The seat according to claim 1, comprising at least one presence sensor, wherein the climate controller or the massager is operated based on the measurement from the at least one presence sensor.

8. A method for managing comfort of an occupant of a vehicle seat, said vehicle seat comprising at least a climate controller and a massager suited for acting on a part of the body of the occupant of the seat, said method comprising the steps of:

getting at least one measurement of at least one biomarker contained in sweat from the occupant of the seat, from at least one sensor of sweat, wherein at least one first biomarker among said at least one biomarker and at least one second biomarker among said at least one biomarker are measured independently by the at least one sensor of sweat, and wherein the at least one first biomarker is characteristic of an excess of body heat from the occupant, and the at least one second biomarker is characteristic of a stress of the occupant; and operating the climate controller and the massager based on the at least one measurement of the at least one biomarker contained in sweat from the occupant of the seat, wherein the climate controller is operated when said at least one first biomarker is detected and wherein the massager is operated when said at least one second biomarker is detected.

9. The method according to claim 8, wherein the at least one measurement of the at least one biomarker contained in the sweat from the occupant of the seat is done with at least one sweat sensor adapted to be disposed directly in contact with the skin of the occupant.

10. The method according to claim 8, wherein the climate controller includes at least one of means of ventilation, means of heating, or means of cooling.

11. The method according to claim 8, wherein the seat further comprises at least one presence sensor, wherein the climate controller or the massager is operated based on the measurement from the presence sensor.

12. The method according to claim 8, wherein a plurality of means of action are operated based on the at least one measurement of said at least one biomarker contained in sweat from the occupant of the seat, from the at least one sensor of sweat from the occupant of the seat, and wherein the means of action are disposed in various individualized seat surface areas.

13. The method according to claim 12, wherein the individualized seat surface areas correspond respectively to various parts of the body of the occupant.

14. The method according to claim 8, wherein the at least one measurement of the at least one biomarker contained in the sweat from the occupant of the seat is done with at least one sweat sensor disposed in the seat.

\* \* \* \* \*